United States Patent
Mitrovic

(10) Patent No.: US 10,646,348 B2
(45) Date of Patent: May 12, 2020

(54) ORTHOPEDIC IMPLANT

(71) Applicants: ZM Praezisionsdentaltechnik GmbH, Rostock (DE); Milija Mitrovic, Rostock (DE)

(72) Inventor: Milija Mitrovic, Rostock (DE)

(73) Assignee: ZM Praezisiondentaltechnik GmbH, Rostock (DE)

( * ) Notice: Subject to any disclaimer, the term of this patent is extended or adjusted under 35 U.S.C. 154(b) by 68 days.

(21) Appl. No.: 16/066,117

(22) PCT Filed: Dec. 28, 2016

(86) PCT No.: PCT/DE2016/000441
§ 371 (c)(1),
(2) Date: Jun. 26, 2018

(87) PCT Pub. No.: WO2017/114519
PCT Pub. Date: Jul. 6, 2017

(65) Prior Publication Data
US 2019/0298535 A1    Oct. 3, 2019

(30) Foreign Application Priority Data

Dec. 29, 2015 (DE) .................. 10 2015 016 895

(51) Int. Cl.
*A61F 2/38* (2006.01)
*A61L 27/06* (2006.01)
(Continued)

(52) U.S. Cl.
CPC ............ *A61F 2/3859* (2013.01); *A61L 27/06* (2013.01); *A61L 27/10* (2013.01); *A61L 27/105* (2013.01);
(Continued)

(58) Field of Classification Search
CPC .......... A61F 2/3859; A61F 2002/30733; A61F 2002/30451; A61F 2220/0058;
(Continued)

(56) References Cited

U.S. PATENT DOCUMENTS 5,024,883 A * 6/1991 Singhdeo .......... H01L 23/49805
428/323
5,037,441 A    8/1991 Bouvet
(Continued)

FOREIGN PATENT DOCUMENTS

DE    29 21 529    12/1980
DE    690 16 110    8/1995
(Continued)

OTHER PUBLICATIONS

PCT Examiner Wolfram Lamers, English translation of the International Search Report of the International Searching Authority for International Application PCT/DE2016/000441, dated May 9, 2017, 3 pages, European Patent Office, HV Rijswijk, Netherlands.
(Continued)

*Primary Examiner* — David H Willse
*Assistant Examiner* — Javier G Blanco
(74) *Attorney, Agent, or Firm* — W. F. Fasse

(57) ABSTRACT

An orthopedic implant in the form of a femoral component of a knee endoprosthesis has sliding tribological surfaces formed by inserts of a ceramic material based on zirconium dioxide or aluminum oxide, which are inserted and transition flushly into a metallic base body. The inserts are connected to the base body by a silicate ceramic solder, which is solidified or hardened in a ceramic firing, and by a silicate glass solder. Discharge channels in the metallic base body help to produce a homogeneous glass solder layer and to avoid an excessively intense heat treatment of the solder connection, which could lead to fractures in the titanium
(Continued)

oxide layer of the base body. Because a coating of a softer glass solder may be additionally provided on the sliding tribological surfaces of the inserts, the abrasive wear is further reduced and the service life is further increased.

7 Claims, 2 Drawing Sheets

(51) Int. Cl.
  *A61L 27/10* (2006.01)
  *A61L 27/18* (2006.01)
  *A61L 27/30* (2006.01)
  *A61F 2/30* (2006.01)

(52) U.S. Cl.
  CPC ............... *A61L 27/18* (2013.01); *A61L 27/30* (2013.01); *A61F 2002/30451* (2013.01); *A61F 2002/30733* (2013.01); *A61F 2002/30805* (2013.01); *A61F 2002/30934* (2013.01); *A61F 2220/0058* (2013.01); *A61F 2310/00023* (2013.01); *A61F 2310/00179* (2013.01); *A61F 2310/00203* (2013.01); *A61F 2310/00239* (2013.01)

(58) Field of Classification Search
  CPC .. A61F 2310/00023; A61F 2310/00203; A61F 2310/00239
  See application file for complete search history.

(56) References Cited

U.S. PATENT DOCUMENTS

| | | | | |
|---|---|---|---|---|
| 5,171,282 | A * | 12/1992 | Pequignot | ........... A61F 2/30907 623/20.35 |
| 6,214,051 | B1 | 4/2001 | Badorf et al. | |
| 2005/0112397 | A1 * | 5/2005 | Rolfe | ................... A61C 8/0012 428/593 |
| 2006/0188845 | A1 | 8/2006 | Serafin, Jr. et al. | |
| 2013/0158694 | A1 * | 6/2013 | Rubbed | ................... A61C 5/30 700/98 |
| 2019/0008645 | A1 | 1/2019 | Mitrovic | |
| 2019/0015214 | A1 | 1/2019 | Mitrovic | |

FOREIGN PATENT DOCUMENTS

| | | | |
|---|---|---|---|
| DE | 197 11 628 | 7/1998 | |
| DE | 199 52 918 | 6/2001 | |
| DE | 103 40 059 | 2/2005 | |
| DE | 603 06 739 | 7/2007 | |
| DE | 102011015299 A1 * | 9/2012 | ........... A61C 8/0013 |
| DE | 102011015300 | 9/2012 | |
| DE | 102012014345 | 1/2014 | |
| EP | 2 742 905 | 6/2014 | |
| GB | 2 396 561 | 6/2004 | |
| JP | 05-168693 A | 7/1993 | |
| WO | WO 2012/010899 | 1/2012 | |
| WO | WO 2012/126449 | 9/2012 | |

OTHER PUBLICATIONS

English Translation of PCT Written Opinion of the International Searching Authority for International Application PCT/DE2016/000441, dated May 9, 2017, 7 pages, International Bureau of WIPO, Geneva, Switzerland.

Aurica Zothner et al., "Die Evolution des Abutments" (The Evolution of the Abutment), Quintessenz der Zahntechnik, Quintessenz Verlags, DE, vol. 35, No. 5, Jan. 1, 2009, pp. 2-16, XP002676248, ISSN: 0340-4641, Retrieved from the Internet: URL:http://www.memodent.nl/upload/content/documents/qz_05_2009_zothner.pdf, especially pp. 10-13, with partial English translation, 3 pages.

* cited by examiner

ORTHOPEDIC IMPLANT

FIELD OF THE INVENTION

The invention relates to an orthopedic implant in the form of a knee endoprosthesis with a femoral component that has sliding tribological surfaces formed by ceramic inserts that are inserted and glass-soldered in a metallic base body.

BACKGROUND INFORMATION

In the artificial replacement of a knee joint, the impaired joint surfaces are removed and replaced by two implants that are independent of one another on the tibial and femoral side, that is to say on the upper end of the shin bone (tibia) and on the lower end of the thigh bone (femur). In that regard, the joint surface replacement on the femoral side is served by an implant that, for most known implants, consists either of a special high strength titanium alloy or of a cobalt-chromium alloy, which are cast or forged and thereafter polished. In that regard, the tibial joint side is replaced by an implant consisting of the titanium or cobalt-chrome alloy, and generally a polyethylene insert is secured thereon, which serves as the sliding tribological partner for the femoral component.

Nowadays, the artificial knee joint replacement is a reliable operation, with service lifetimes of the implants of up to 15 years. The most frequent cause of failure is the aseptic implant loosening, which is caused by abrasive wear particles of the tibial polyethylene component, and which can considerably shorten the service lifetime of an implant. The wear particles arise due to the abrasive wear of the polyethylene component, caused by the frictional abrasion with the femoral component. If the wear particles get into the bone-implant interface, biological processes are triggered on the implant-bone boundary surfaces with a cement-free anchoring or on implant-bone cement-bone boundary surfaces with a cemented anchoring, wherein these biological processes can lead to a progressive local destruction of the bone and thus finally to a loosening of the implants. If the polyethylene component of the tibia is completely consumed or used up, as a result it can additionally cause an abrasive wear of the metallic tibia plateau located thereunder, and thus allergic reactions to the metal ions that are thereby released.

Besides the metallic knee endoprostheses, a zirconium-niobium alloy is utilized under the trade name Oxinium®, of which the femoral component is transformed into a zirconium oxide ceramic in a heat treatment process at approximately 500° C., which, so to speak, represents a coating of zirconium dioxide. Furthermore, implants have become known, in which a femoral component of a mixed ceramic (BioloxDelta®) is utilized. The abrasive wear of the polyethylene is reduced by the use of this femoral component which is available in the market, in comparison to metal/polyethylene sliding tribological pairings, and in this manner the durability of the knee endoprosthesis is lengthened. However, the high manufacturing costs of the Oxinium components as well as the brittleness and the inadequate adhesion of the ceramic components on the bone cement or on the bone are to be regarded as disadvantages of these known components.

Beside these known implants, an implant of the above mentioned type in the form of a knee endoprosthesis of a metallic material has also become known from the DE 10 2011 015 300 A1, in which the sliding tribological surfaces of the femoral component already consist of a ceramic material, and in which the connection or joint between the inserts and the metallic base body of the femoral component is produced via a silicate glass solder.

SUMMARY OF THE INVENTION

An object of at least one embodiment of the invention is to further develop such an implant in such a manner so that the friction and therewith the abrasive wear between the femoral component and the polyethylene sliding tribological partner is as small as possible in comparison to the typically utilized sliding tribological pairings, and simultaneously the adhesion of the femoral component in the femur bone is increased.

The above object can be achieved by an embodiment of the invention in that the connection or joint between the inserts and the metallic base body is produced via a silicate first glass solder that is solidified or hardened in a ceramic firing, as well as via a second glass solder that melts at a temperature higher than a melting temperature of the first glass solder yet below the melting temperature of the metallic base body. For an optimal osseointegration of the implant, it is further advantageous if the base body of the femoral component, which consists of a metallic material and which is to be connected or joined with the thigh bone, preferably consists of a high strength titanium alloy with a thermal expansion coefficient value of approximately 10.5.

BRIEF DESCRIPTION OF THE DRAWINGS

In the following, the invention will be explained in further detail in connection with an example embodiment that is illustrated in the drawing. It is shown by.

DETAILED DESCRIPTION OF EXAMPLE EMBODIMENTS OF THE INVENTION

Figure 1:
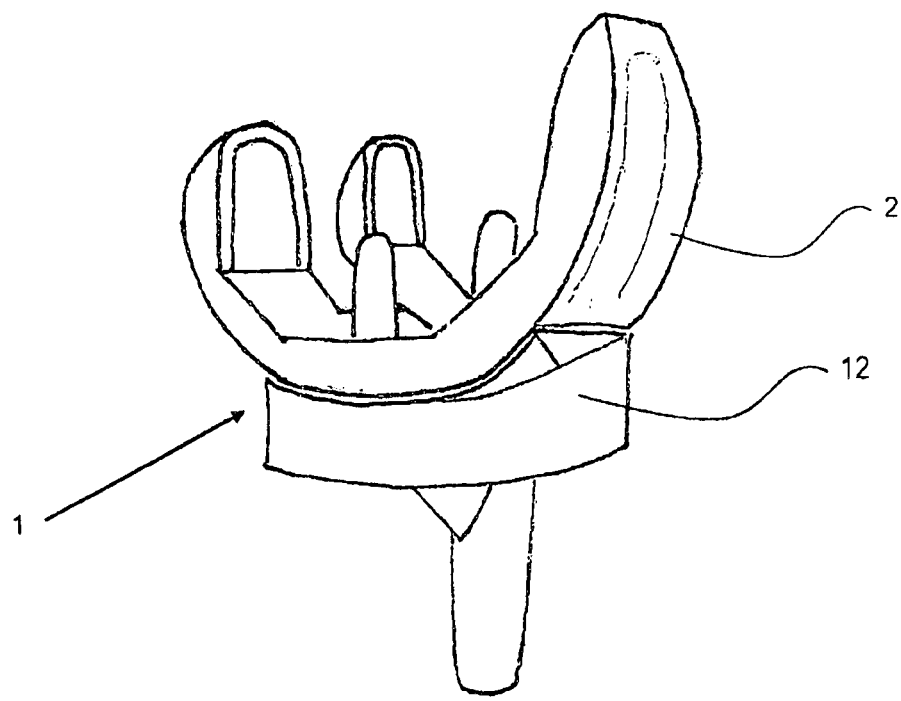
FIG. 1 a knee endoprosthesis according to the prior art in a perspective illustration, FIG. 2 a schematic illustration of a femoral knee joint implant according to the invention fixed on a thigh bone, FIG. 3 a schematic sectional illustration of an arrangement of base body and insert for the femoral component of a knee endoprosthesis according to FIG. 2, and FIG. 4 a schematic illustration of an enlarged partial area of an insert according to FIG. 3 after a longer service life duration of a knee endoprosthesis.

The drawing in FIG. 1 shows a knee endoprosthesis 1 according to the prior art in a perspective illustration. The implant is formed by a femur component with a base body 2 that consists of a ceramic material, as well as a tibia component 12 of which at least the area facing toward the femur component consists of polyethylene.

Figure 2:
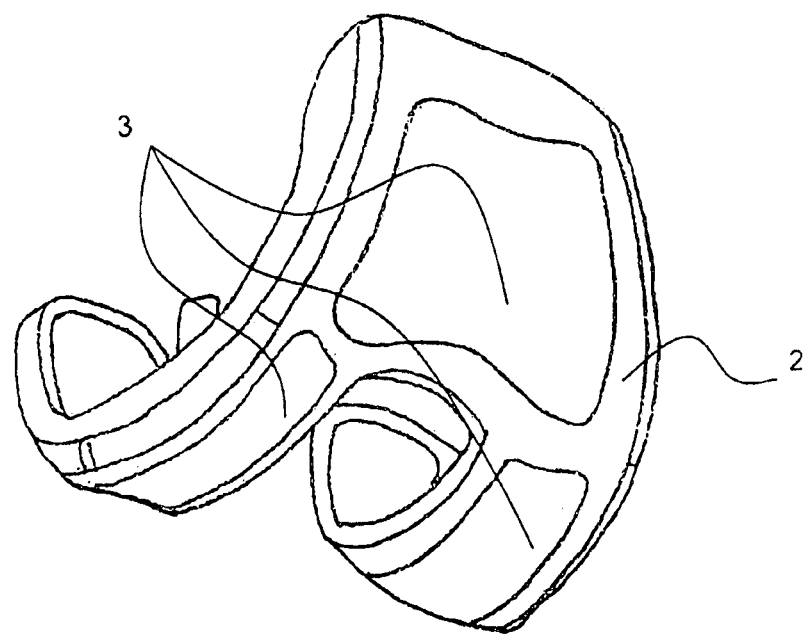

In comparison, FIG. 2 shows a femur component according to an embodiment of the present invention, with sliding tribological surfaces that are formed by inserts 3 of a ceramic material that are inserted in a base body 2. In the case of the example embodiment described here, zirconium dioxide was used for producing these inserts 3, but in the same manner the inserts 3 can however alternatively consist of an aluminum oxide ceramic or of a mixture of these two ceramics.

Figure 3:
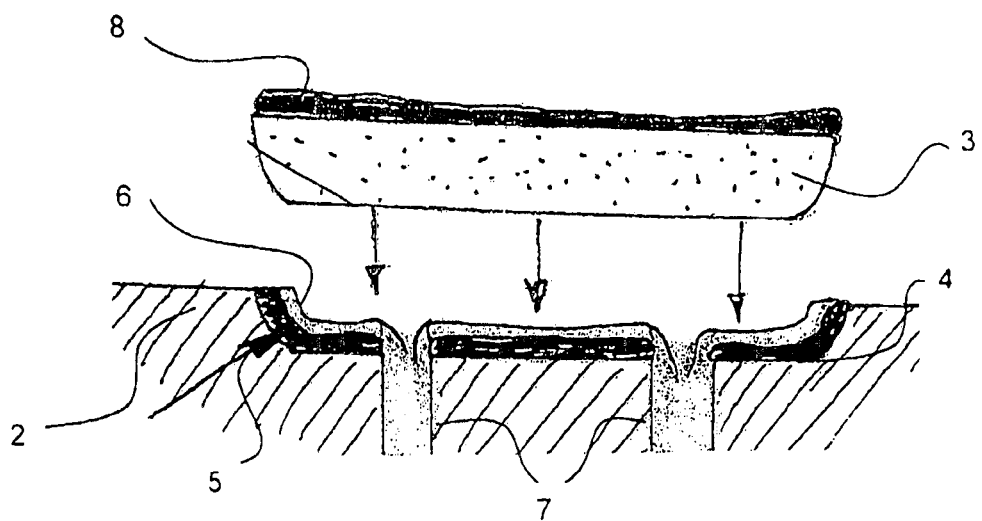

The ceramic inserts 3 are integrated in the manner of inlays in allocated "tub or trough shaped" receiver recesses 4 of a metallic base body 2 of the femoral component, wherein the base body 2 is of a titanium material, particularly of the high strength titanium alloy Ti-6A1-4V (titanium grade 5) in the case of the embodiment illustrated here, so that the inserts 3 transition in a flush or stepless manner into the base body 2, and so that no offset or step edges are formed. In view of the background that titanium as such has a rough surface, and furthermore forms an oxide layer during heating, which prevents a homogeneous soldering, therefore the titanium must at first be pre-treated by a special firing process. In that regard, the ceramic inserts 3 are secured by a silicate glass solder, which is solidified or hardened in a ceramic firing and in this manner securely connects or joins these ceramic inserts 3 with the metallic base body 2. This is indicated by three arrows on the insert 3 shown in FIG. 3.

This pre-treatment is absolutely necessary, because the size of the objects to be soldered and the heat treatment would cause a negative influence on the solder connection or joint, such as for example fractures in the titanium oxide layer. The pre-treatment is generally achieved by means of an airbrush method, in which the layer of the silicate glass solder is uniformly sprayed on and subjected to the subsequent firing process. Through the firing process there arises a solder layer 5, which both binds titanium oxide as well as smooths-out or uniformalizes the roughness of the titanium, and thus offers the optimal base for the subsequent soldering process.

In order to produce a homogeneous glass solder layer 6 on this solder layer 5, it requires a proper layer thickness between, in this case, 0.1 and 0.3 mm, as well as the presence of suitable withdrawal or discharge channels 7, which together provide the precondition for a homogeneous flow of the glass solder 6 in this area. The withdrawal or discharge channels 7 in the titanium shown in FIG. 3 in that regard effectuate a capillary effect, which allows excess glass solder 6 to flow away homogeneously and reliably prevents the formation of fractures in the titanium oxide layer.

After implantation has been carried out, the inserts 3 of ceramic reproduce or imitate the outer shape of conventional metallic femur components in the sliding tribological surface and significantly reduce the abrasive wear between the femoral component and the polyethylene of the tibia component 12. It is this reduced abrasive wear of the sliding tribological partners that reduces the risk of the particle-induced aseptic loosening and leads to longer service lifetimes of the implants. Because a coating of a glass solder 8, which in this case is softer, is provided also on the upper surfaces of the sliding tribological surfaces of the ceramic inserts 3 facing away from the metallic base body 2, the abrasive wear is further reduced and the service life of the implant is further increased. Bored holes serving as withdrawal or discharge channels 7 and a homogeneous distribution of the pre-coating 5 are not necessary here, because the glass solder 8 is captured or retained in the ceramic or flows out of it.

Figure 4:
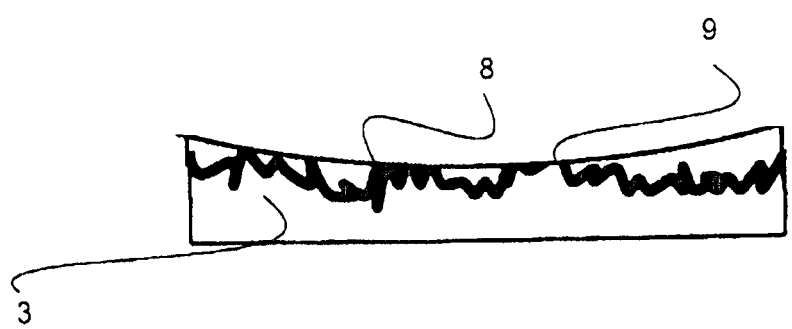

Because the glass solder coating 8 is embodied slightly softer and thus more resilient or yielding than the ceramic material of the insert 3 in the sliding tribological surface, therefore during the course of the service lifespan of the knee endoprosthesis, a small abrasive wear removal of the coating 8 of the inserts 3 in the sliding tribological surface of the femur component is additionally also possible, as is finally shown schematically in FIG. 4. Whereas an abrasive wear of the metal ions can be observed in this area in many conventional constructions, instead of that, in the case of the present embodiment of the invention there arises merely a comparatively harmless abrasive wear 9 of the outwardly lying coating 8 applied on the ceramic inserts 3 of the femur component, wherein the coating 8 is formed of a softer glass solder 8, which essentially contains silicon.

The invention claimed is:

1. A femoral component of a knee endoprosthesis, the femoral component comprising:
a metallic base body comprising a metallic base material;
a sliding surface member comprising a ceramic member that consists of a ceramic material that comprises at least one of zirconium dioxide and aluminum oxide; and
a joining layer between the metallic base body and the ceramic member, comprising a first layer of a first glass solder and a second layer of a second glass solder between adjoining surfaces of the metallic base body and the ceramic member;
wherein:
the joining layer joins the ceramic member to the metallic base body;
the sliding surface member has an outer sliding tribological surface that faces away from the metallic base body and that is configured and adapted to make sliding contact with a tibial component of a knee endoprosthesis;
the metallic base body has a solder discharge channel extending into the metallic base body from the adjoining surface thereof;
the metallic base body has a recess, wherein the adjoining surface of the metallic base body bounds the recess, and wherein the sliding surface member is received in the recess with the adjoining surface of the ceramic member in the recess adjacent to the adjoining surface of the metallic base body and with the joining layer between the adjoining surfaces of the ceramic member and the metallic base body;
the first glass solder has a first melting temperature, the second glass solder has a second melting temperature, the metallic base material has a third melting temperature, and the second melting temperature is higher than the first melting temperature and lower than the third melting temperature; and
the joining layer is produced to join the ceramic member to the metallic base body by applying the first glass solder onto the adjoining surface of the metallic base body, solidifying or hardening the first glass solder by performing a ceramic firing to form the first layer, and thereafter applying the second glass solder onto the first layer and firing the second glass solder to form the second layer between the first layer and the adjoining surface of the ceramic member.

2. The femoral component according to claim 1, wherein the sliding surface member is received entirely flushly within the recess of the metallic base body so that the outer sliding tribological surface of the sliding surface member transitions in a stepless manner to a surface of the metallic base body.

3. The femoral component according to claim 1, wherein the second glass solder extends from the second layer of the joining layer also into the solder discharge channel.

4. The femoral component according to claim 1, wherein the solder discharge channel is configured and dimensioned to cause a capillary effect with respect to the second glass solder during the firing thereof.

5. The femoral component according to claim 1, wherein the sliding surface member further comprises a surface coating of a third glass solder on an outer surface of the ceramic member facing away from the metallic base body, the surface coating of the third glass solder forms the outer sliding tribological surface, and the third glass solder of the surface coating is softer than the ceramic material of the ceramic member.

6. A method of making the femoral component according to claim 1, comprising the steps:
   a) applying the first glass solder onto the adjoining surface of the metallic base body;
   b) after the step a), performing the ceramic firing to solidify or harden the first glass solder to form the first layer on the adjoining surface of the metallic base body;
   c) after the step b), applying the second glass solder onto the first layer;
   d) after the step c), placing the ceramic member with the adjoining surface thereof onto the second glass solder;
   e) after the step d), performing the firing of the second glass solder to form the second layer of the second glass solder that joins the adjoining surface of the ceramic member to the adjoining surface of the metallic base body via the first layer of the first glass solder on the adjoining layer of the metallic base body.

7. The femoral component according to claim 1, wherein the metallic base body further comprises an oxide layer on the metallic base material, which oxide layer forms the adjoining surface of the metallic base body, and wherein the first glass solder of the first layer of the joining layer binds with the oxide layer of the metallic base body at the adjoining surface and smooths-out or uniformalizes a roughness of the adjoining surface.

* * * * *